(12) United States Patent
Huang et al.

(10) Patent No.: US 8,153,811 B2
(45) Date of Patent: Apr. 10, 2012

(54) LATENT FLUORIMETRIC INDICATOR FOR BIOLOGICAL ANALYTES DETERMINATION AND THE PREPARATION METHOD THEREOF

(75) Inventors: Sheng-Tung Huang, Taipei (TW); Yi-Xiang Peng, Sanchong (TW)

(73) Assignee: National Taipei University of Technology (TW)

( * ) Notice: Subject to any disclaimer, the term of this patent is extended or adjusted under 35 U.S.C. 154(b) by 485 days.

(21) Appl. No.: 12/366,975

(22) Filed: Feb. 6, 2009

(65) Prior Publication Data

US 2010/0047839 A1 Feb. 25, 2010

(30) Foreign Application Priority Data

Aug. 19, 2008 (TW) ................. 97131646 A

(51) Int. Cl.
*C07D 405/04* (2006.01)
(52) U.S. Cl. ..................................... 548/159
(58) Field of Classification Search .................. 548/159
See application file for complete search history.

(56) References Cited

PUBLICATIONS

Huang et al., Biosensors and Bioelectronics (Mar. 4, 2008), 23(12), pp. 1793-1798.*

* cited by examiner

*Primary Examiner* — Laura L. Stockton
(74) *Attorney, Agent, or Firm* — Schmeiser, Olsen & Watts, LLP

(57) ABSTRACT

The present invention provides a sensitive fluorimetric indicator for analytes determination in the oxygen-insensitive DT-diaphorase-coupled dehydrogenases assay by omitting NADH, which is generated by reaction in the presence of analytes, which presents to the applicability as a biosensor for future clinical diagnostic. Furthermore, the novel long-wavelength latent fluorimetric indicator is also a user-friendly probe for monitoring DT-diaphorase activity. The fluorescence signal revealed by this process is specific and exhibited in the near red spectrum region.

2 Claims, 9 Drawing Sheets

Figure 1:
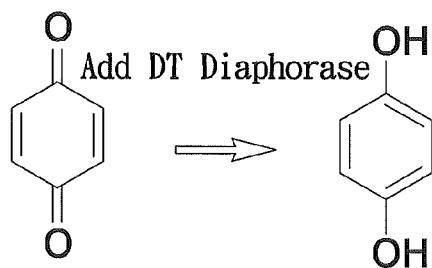

LATENT FLUORIMETRIC INDICATOR FOR BIOLOGICAL ANALYTES DETERMINATION AND THE PREPARATION METHOD THEREOF

BACKGROUND OF THE INVENTION (a) Field of the Invention

The present invention relates to a novel long-wavelength latent fluorimetric indicator for the monitoring DT-diaphorase activity and the measurement of trace living biological samples with high sensitivity.

(b) Description of the Prior Art

Redox reaction with a fluorimetric redox indicator for qualitative or quantitative determining analytes had been widely applied in the diagnostic applications. In this case, an oxidizing or reducing system directly acts on the fluorimetric redox indicator or via a mediator. The presence of analytes results in the reduction or oxidation of the fluorimetric redox indicator which allows for a quantitative determination; however, the known oxygen-dependent fluorimetric detection reagents for determining analytes have drawbacks. For example, the fluorimetric methods of glucose determination with glucose oxide (GOD)-peroxidase (POD)-fluorimetric indicators system are well known. The fluorescent indicating reactions in these methods are based by detecting $H_2O_2$ which generated through GOD-catalyzed oxidation of glucose with presence of $O_2$, and the detecting of $H_2O_2$ is catalytically supported by POD. POD with presence of $H_2O_2$ oxidizes the fluorimetric indicators resulting in the revealing or diminishing of their fluorescence; however, this catalytic reaction is prone to interference by electron donors such as urea or bilirubin. Although the redox indicators that directly or via a mediator accept an electron from an oxidizing enzyme instead of oxygen are preferred, they also have other problems. For instance, resazurin (U.S. publication No. 20040234945 and U.S. Pat. No. 5,912,139), transition metal Os and Ru complexes (Ryabov et al., JBIC 4 (1999), 175-182; Woltman et al, Anal. Chem. 71 (199), 1504-1512) are oxygen-independent fluorescent indicators for glucose. In the case of transition metals, their fluorescence efficiency varies with the oxygen content of the sample. On the other hand, resazurin is a fluorimetric redox indicator that accepts an electron from an oxidizing enzyme via mediators. The non-fluorescent resazurin is converted into fluorescence-developing resorufin by the redox reaction. The emission band of resorufin strongly overlaps the absorption band of non-reacted resazurin which considerably reduces the sensitivity of the analyte determination. Furthermore, the fluorescence-developing resorufin can be further reduced in the redox system to yield a nonfluorescent product which lead to the uncertainty of the analytes determination. Chromogenic indicators with high sensitivity and minimum interference are critical for the successful implementation of fluorimetric redox assays.

Fluorescence has long been viewed as a powerful tool for basic research in the biological sciences, the development of new drugs, the assurance of food safety and environmental quality and the clinical diagnosis of diseases due to its high resolution and sensitivity. Lately, there is a rapidly growing interest in the development of fluorophores with high selectivity for diagnostic applications. Latent fluorophores are stable molecules with intense fluorescent that are revealed by a user-designated chemical reaction. They are especially useful agents for diagnostic applications because of their unique selectivity and minimal interference from the probe concentration, excitation intensity and emission sensitivity. Elegant designs of molecules that release fluorescent coumarin or rhodamine derivatives upon activation by enzymes had been developed as sensitive tools for monitoring specific enzymatic reactions in diagnostic applications.

The paper by Huang's group describes the use of the trimethyl-lock reaction in designing a benzoquinone rhodamine latent fluorophore (BQRh) for direct monitoring of the activity of DT-diaphorase (DTD). (Huang et al. 8 JOC (2006) 265-268). DTD is a flavoprotein catalyzes the two-electron reduction of various quinones, quinone epoxide, and aromatic nitro-compounds, using NAD(P)H as an electron donor. BQRh also is a sensitive fluorimetric indicator for analytes determination in the oxygen-insensitive DTD-coupling assay by including the corresponding dehydrogenases and $NAD^+$, which is convert to NADH by reaction in the presence of analytes. The BQRh consists of a trimethyl-lock component inserted between a rhodamine dye and an enzyme-reactive group (FIG. 2); upon reduction of the benzoquinone moiety in BQRh by DTD in the presence of NADH, the highly reactive phenol was generated followed by rapid lactone formation with the concomitant release of rhodamine. However, the benzoquinone moiety in BQRh exhibited a reduction in affinity for the active site of DTD compared to other DTD-targeted benzoquinone anticancer agents. That is because the steric interference from the nearby bulky rhodamine dye attributed to this reduction in the affinity which considerably reduces the sensitivity of the analytes determination. In addition, many biological samples exhibit fluorescence, typical in the blue and near rhodamine fluorescence region of the spectrum; thus interfere with the measurement of the fluorescence.

DESCRIPTION OF THE INVENTION

The invention describes the new design and preparation of a new latent fluorimetric indicator to rectify the previous designing drawbacks. The present invention redesigns the prior latent fluorophore, BQRh, by extending the separation between the benzoquinone moiety and the bulky fluorescent dye to minimize the steric interference in FIG. 3. Furthermore, the new latent fluorimetric indicator incorporates a masked long wavelength fluorescence dyes to enhance the sensitivity of the detection by avoided the background fluorescence signal generating from the biological samples. The fluorescent signal is revealed through series of tandem reactions in FIG. 3. The initiating of the trimethyl-lock cyclization reaction was through reducing the quinone moiety in new latent fluorimetric indicator by DTD in the presence of NADH to generate highly reactive phenol. The highly reactive phenol undergoes the trimethyl-lock lactone formation to yield the lactone with a concomitant released of the corresponding highly nucleophilic amine (not shown). The corresponding highly nucleophilic amine attacks the carbamate moiety in highly reactive phenol to form the cyclic urea with simultaneous release of the fluorogenic coumarin.

The present invention discloses the preparation procedures of the latent benzoquinone coumarin fluorimetric indicator and its application as a fluorimetric indicator for analytes determination. Various dehydrogenases oxidize their substrates with $NAD^+$ or $NADP^+$ as the electron acceptors to yield NADH or NADPH which could be utilized by DTD to catalyze the release of the fluorogenic coumarin. The present invention provides a sensitive fluorimetric indicator for analytes determination in the oxygen-insensitive DTD-coupling assay by including the corresponding dehydrogenases and omitting NADH, which is generated by reaction in the presence of analytes in FIG. 5.

The present invention is a method for detecting an analyte by a redox reaction and a fluorimetric determination, characterized in that a sample containing the analyte is contacted with a detection reagent which contains the latent fluorimetric indicator has the general structure of Eq. (1):

In latent fluorimetric indicator of the present invention, wherein the replaceable fluorophore structure shown as Eq. (1), the preferred structure could be the structure shown in Eq. (2):

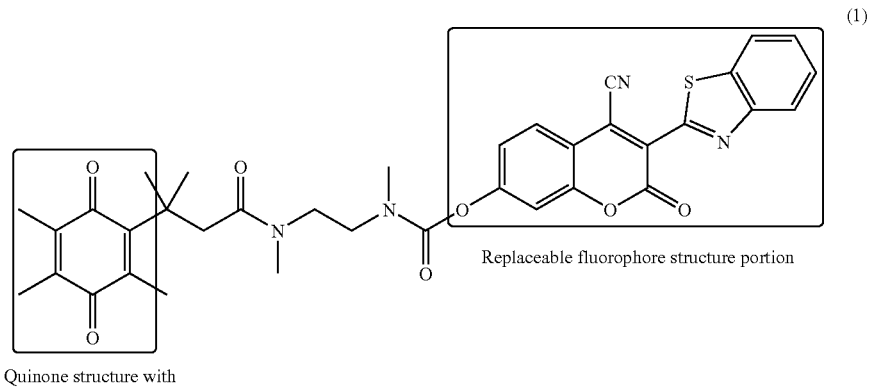

The latent fluorimetric indicator of the present invention contains fluorophore part wherein the said fluorophore part could be either coumarin or other long wavelength fluorescent analogues. And the measurement method could be carried out by the instant monitoring of the assay system. The best excitation wavelength of the fluorogenic probe is about 500 nm, and the best emission wavelength is 595 nm. But the best excitation wavelength and the emission wavelength lie between 530 nm and 730 nm. The changes of the fluorescent intensity could be measured to reflect the concentration variation of the object under test.

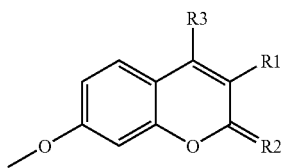

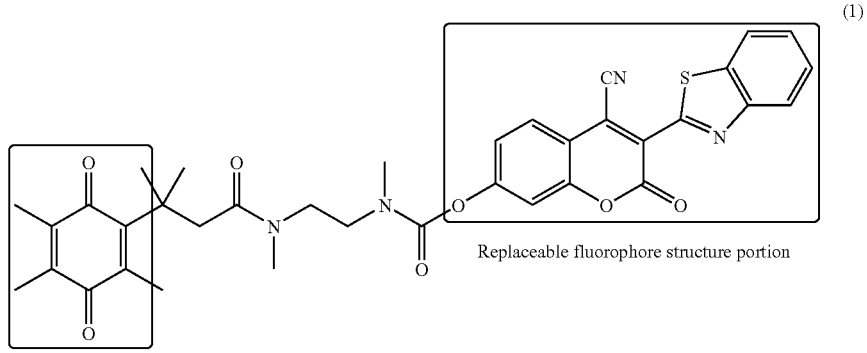

wherein R1 could be any one of the functional group including

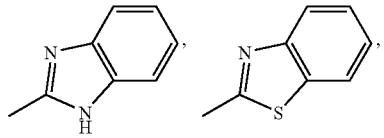

COOH, H, or Cl; R2 could be any one of the functional group including NH, or O; and R3 could be any one of the functional group including H, or $CH_3$.

In the fluorogenic probe of the present invention, wherein the replaceable fluorophore structure shown as Eq. (1) also could be replaced by the structure shown in Eq. (3) or Eq. (4):

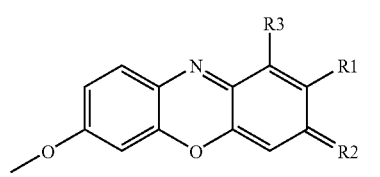
(3)

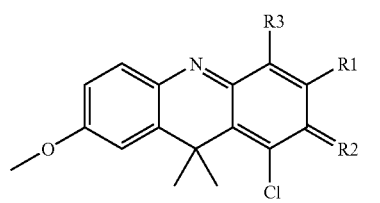
(4)

wherein R1 could be any one of the functional group including

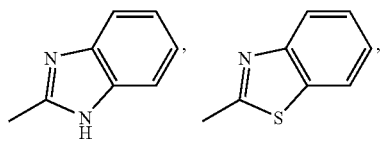

COOH, H, or Cl; R2 could be any one of the functional group including NH, or O; and R3 could be any one of the functional group including H, or $CH_3$.

In latent fluorimetric indicator of the present invention, wherein the quinone structure shown as Eq. (1) could be replaced as shown in Eq. (5) or Eq. (6):

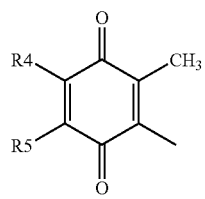
(5)

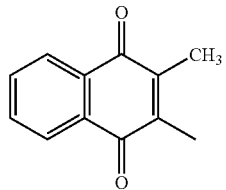
(6)

wherein R4 and R5 could be any one of the functional group including COOH, H, Cl, $CH_3(CH_2)_n$, and n=0 to 9.

The general structure of Eq. 1 as describe above is the preferred reagent for detecting an analyte by a redox reaction and a fluorimetric determination.

Another aspect of the invention is the quinone reduction enzyme which initiated the unmasking of the latent fluorimetric indicator could be the protein series and its similarities, amino acid and its similarities. Among the aforesaid enzymes the DT Diaphorase is preferred.

Figure 5:
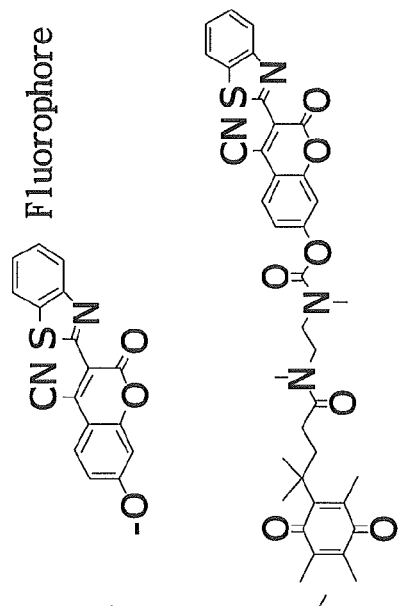
Figure 5:
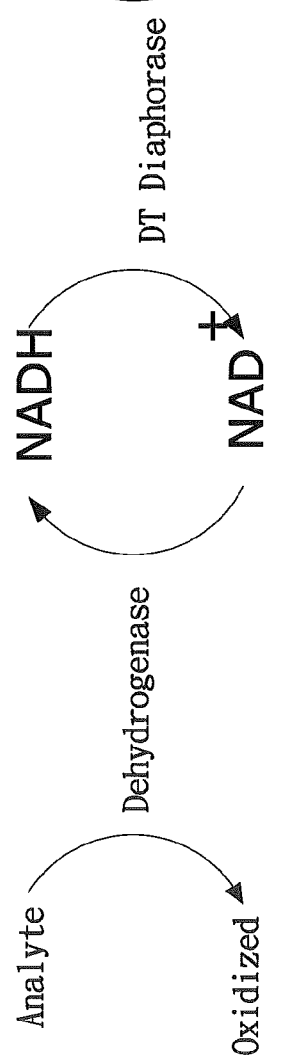

The present invention is suitable for detecting any analytes that can be determine by a redox reaction. The analytes to be determined of the said measuring method could be ethanol, 1-propanol, 2-propanol, cyclohexanol, 2-methyl-1-propanol, 1-heptanol and other primary or secondary alcohol, formaldehyde, acetaldehyde, propyl aldehyde and other primary or secondary aldehyde, lactate, pyruvate, pyruvate, α-ketoglutarate, isocitrate, L-malate, glucose-6-phophate, hydroxybutyrate or any other composition commonly found in the biological samples that have the corresponding dehydrogenase for the redox reaction. And the fluorimetric determination reaction sequences is shown in FIG. 5, wherein each analyte stated above could be combined with the corresponding dehydrogenases, $NAD^+$, or $NADP^+$ and co-enzyme to oxidize the analyte and reduce the $NAD^+$ or $NADP^+$. The enzymes for engaging dehydrogenation action with analytes could be alcohol dehydrogenase, aldehyde dehydrogenase, lactate dehydrogenase, pyruvate dehydrogenase, α-ketoglutarate dehydrogenase, isocitrate dehydrogenase, L-malate dehydrogenase, glucose-6-phophate dehydrogenase, hydroxybutyrate dehydrogenase or any other dehydrogenase composition commonly used in biological assay. Upon the completion on the oxidation of the analytes reaction as shown in FIG. 5, the electrons from the analytes are transferred to the $NAD^+$ or $NADPH^+$ to yield NADH or NADPH respectively. The electrons in NADH or NADPH could then be utilized by the quinone reduced enzyme and DT diaphorase to reduce the quinone moiety of the latent fluorimetric probe in present invention. The reduction of the quinone moiety of the latent fluorimetric probe in present invention initiates a sequence of cascades reaction to release the cloaked fluorophore. Irradiating the uncloaked fluorophore with corresponding excitation wavelength reveals a fluorescence signal. By using the latent fluorimetric probe of the present invention, the intensity of the resulting of the fluorescence signal generated by above describe reaction sequences is directly proportional to the concentration of the analytes.

In addition to the latent fluorimetric probe, the reagent according to the invention can also contains other components selected from enzymes, coenzymes, auxiliary substance, buffers, and mediators.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF ILLUSTRATIONS

FIG. 1 Reaction scheme of quinone reduction by DT Diaphorase and NADH

Figure 2:
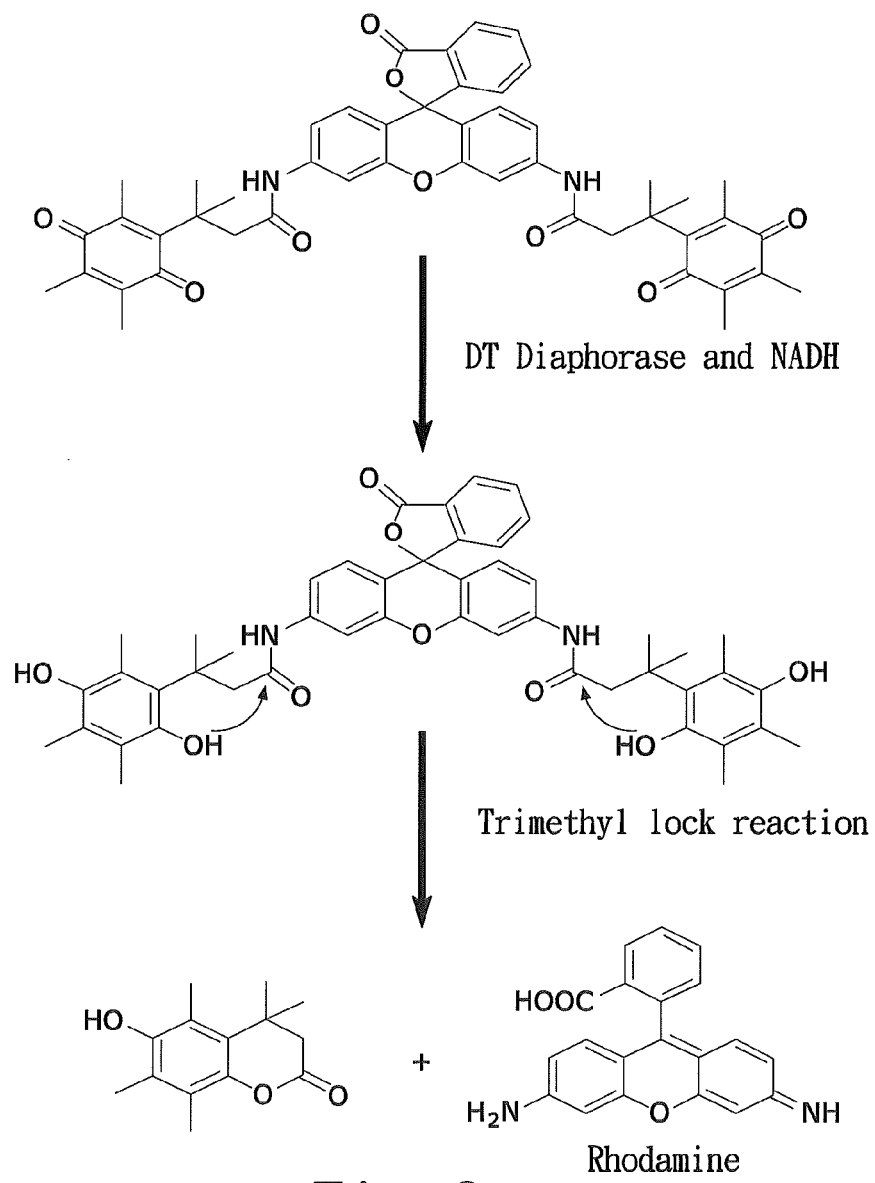
Figure 3:
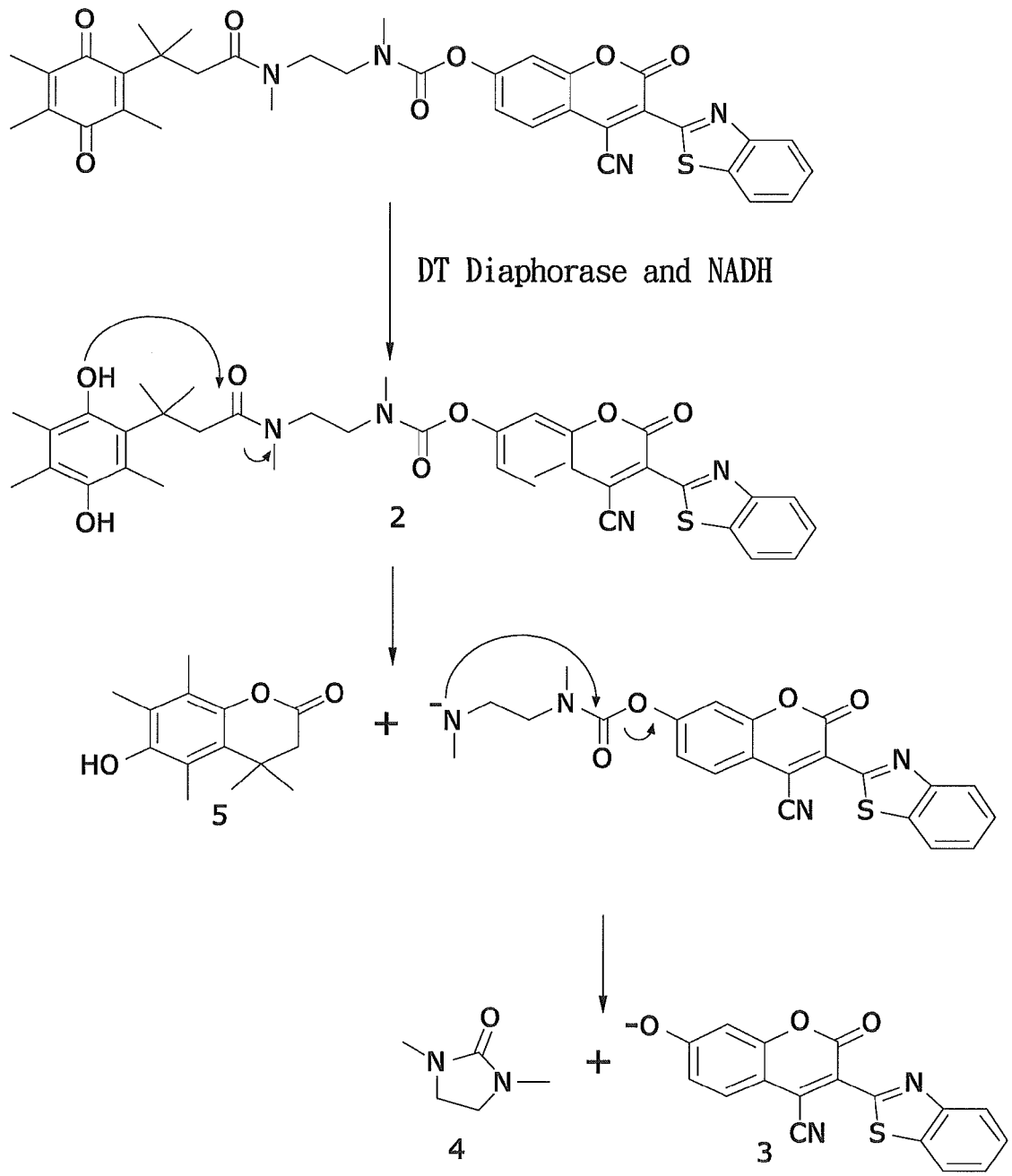
Figure 4:
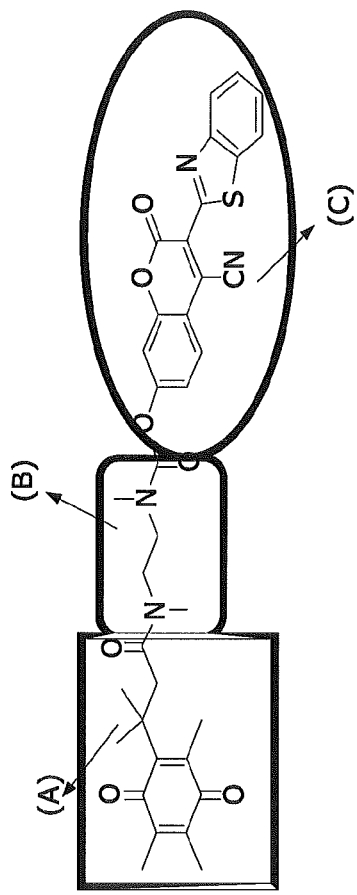
Figure 6:
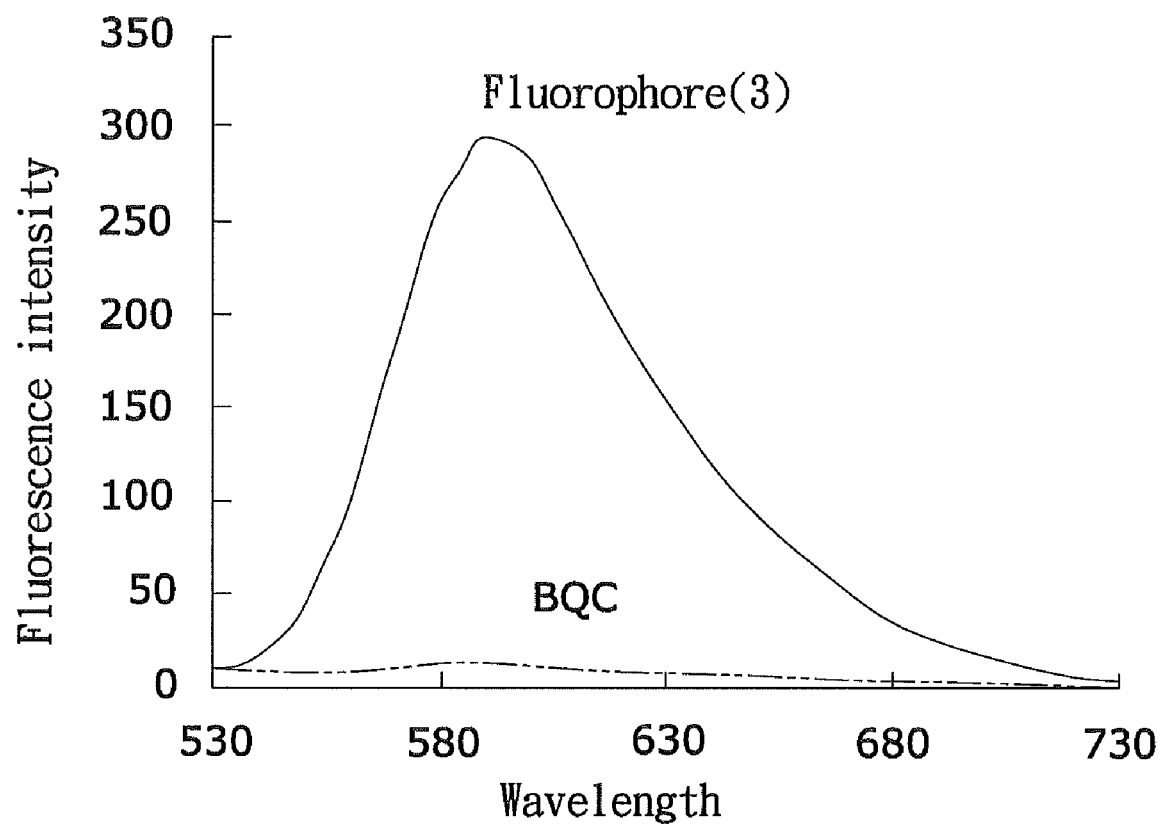

FIG. 2 Reaction scheme of the fluorogenic rhodamine revealed from BQRh reaction mechanism in prior art FIG. 3 Reaction scheme of the fluorogenic coumarin fluorophore revealing reaction mechanism in the present invention FIG. 4 Latent fluorimetric probe structure and functional groups according to the present invention
  (A): Increase the affinity toward enzyme
  (B): Reduce steric barrier
  (C): Long wavelength fluorophore FIG. 5 Reaction scheme of the analytes determination in the oxygen-insensitive DTD-coupling assay by including the latent fluorimetric indicator used in the present invention, corresponding dehydrogenases and $NAD^+$ FIG. 6 Fluorescent spectra of the latent fluorimetric indicator used in the present invention and the fluorogenic coumarin fluorophore (3)

Figure 7:
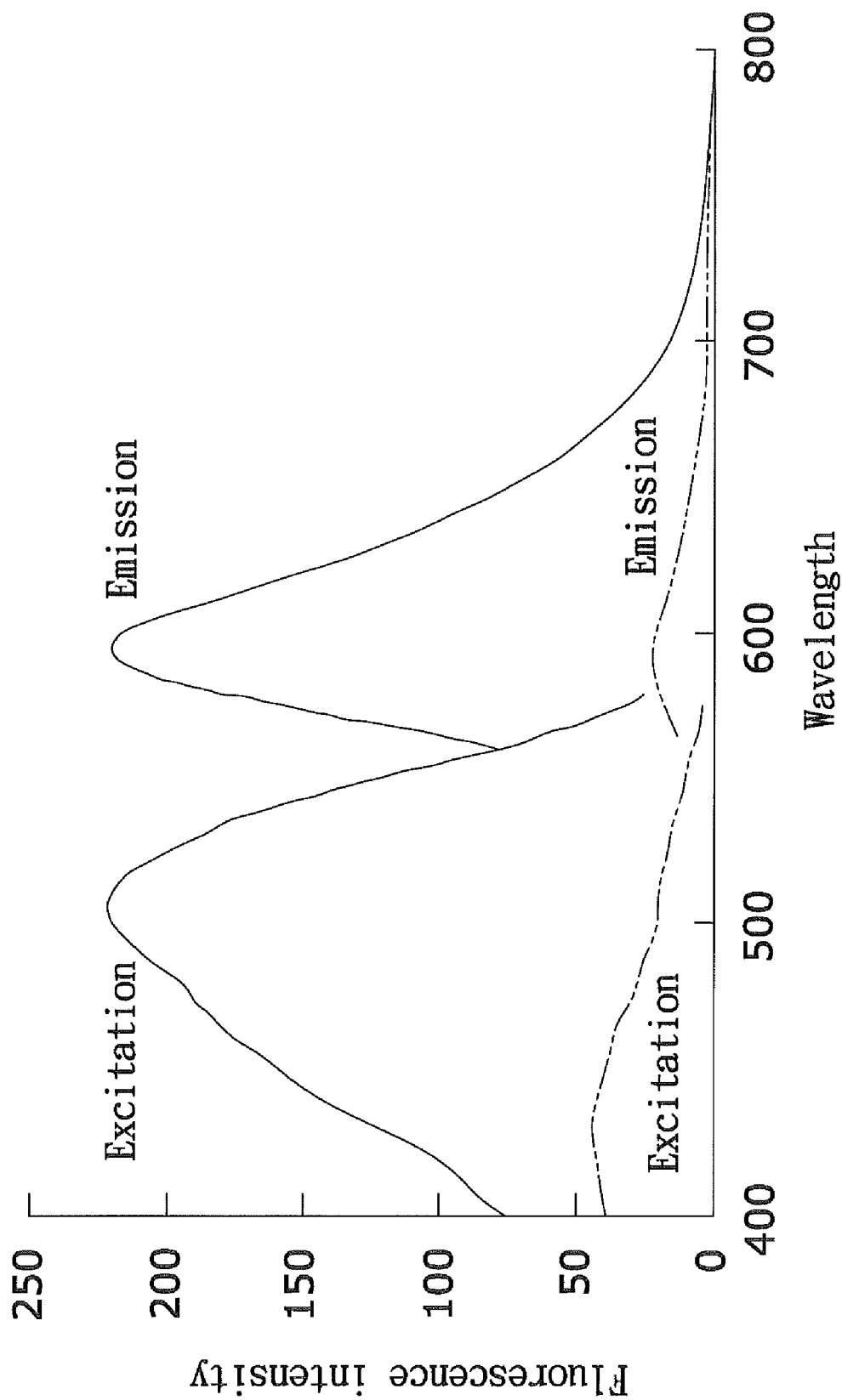
Figure 8:
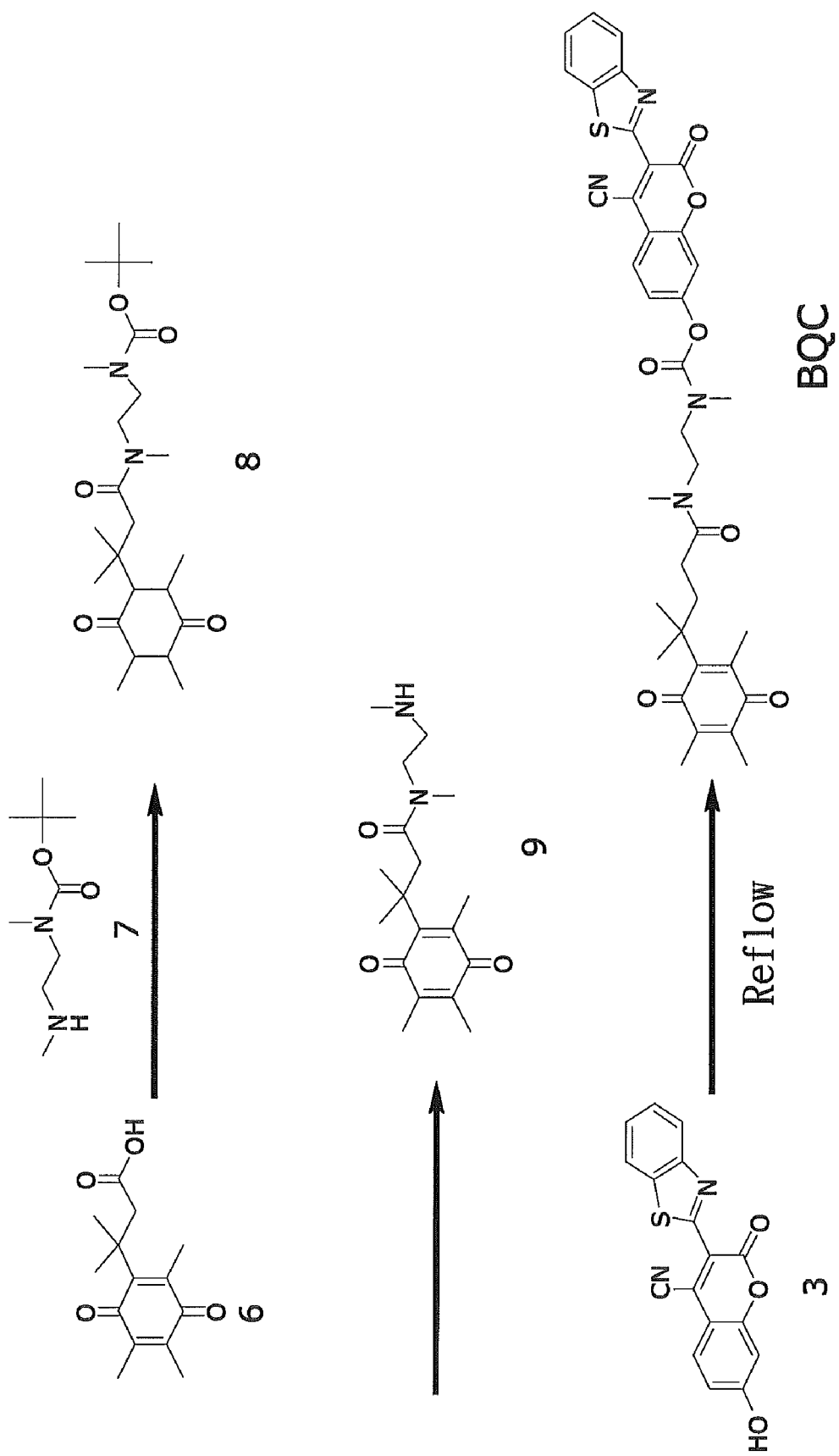
Figure 9:
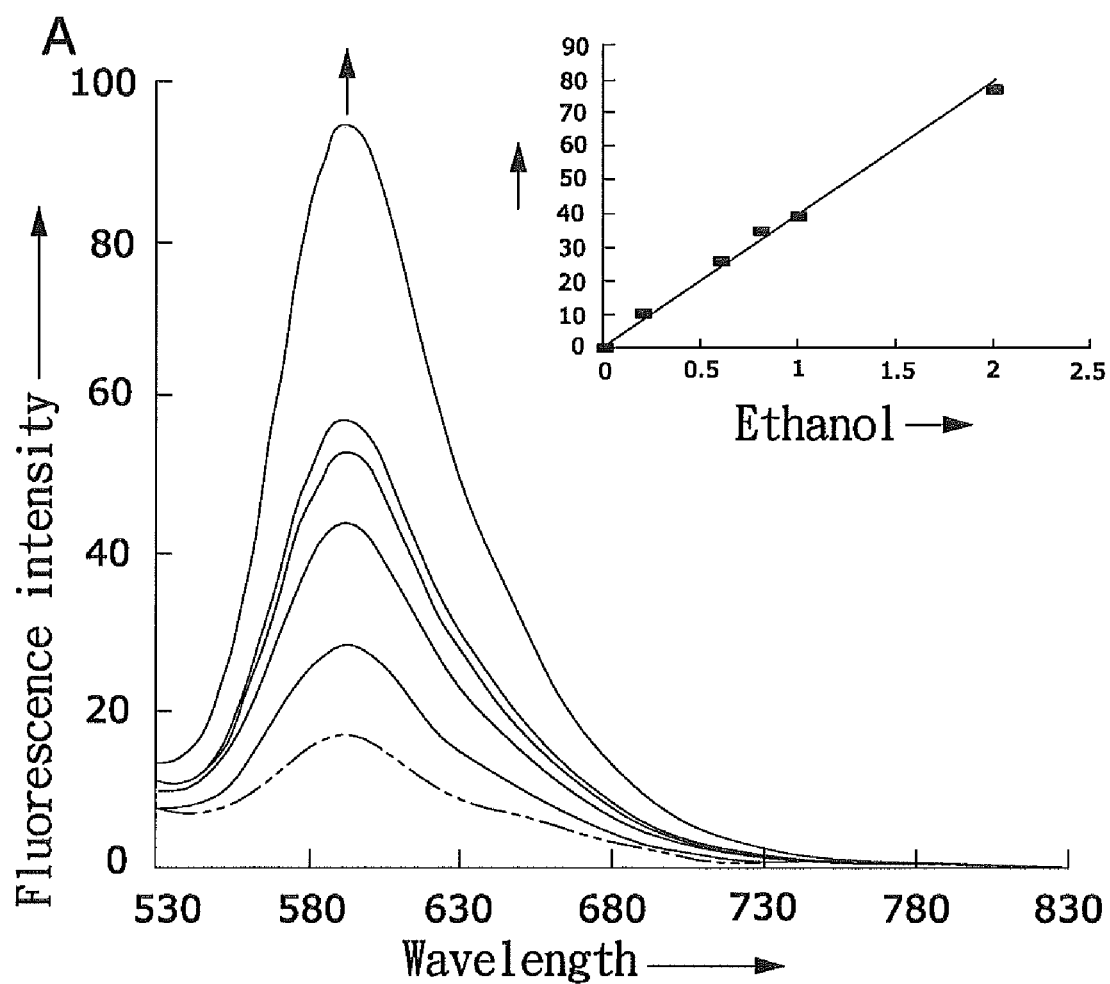
Figure 10:
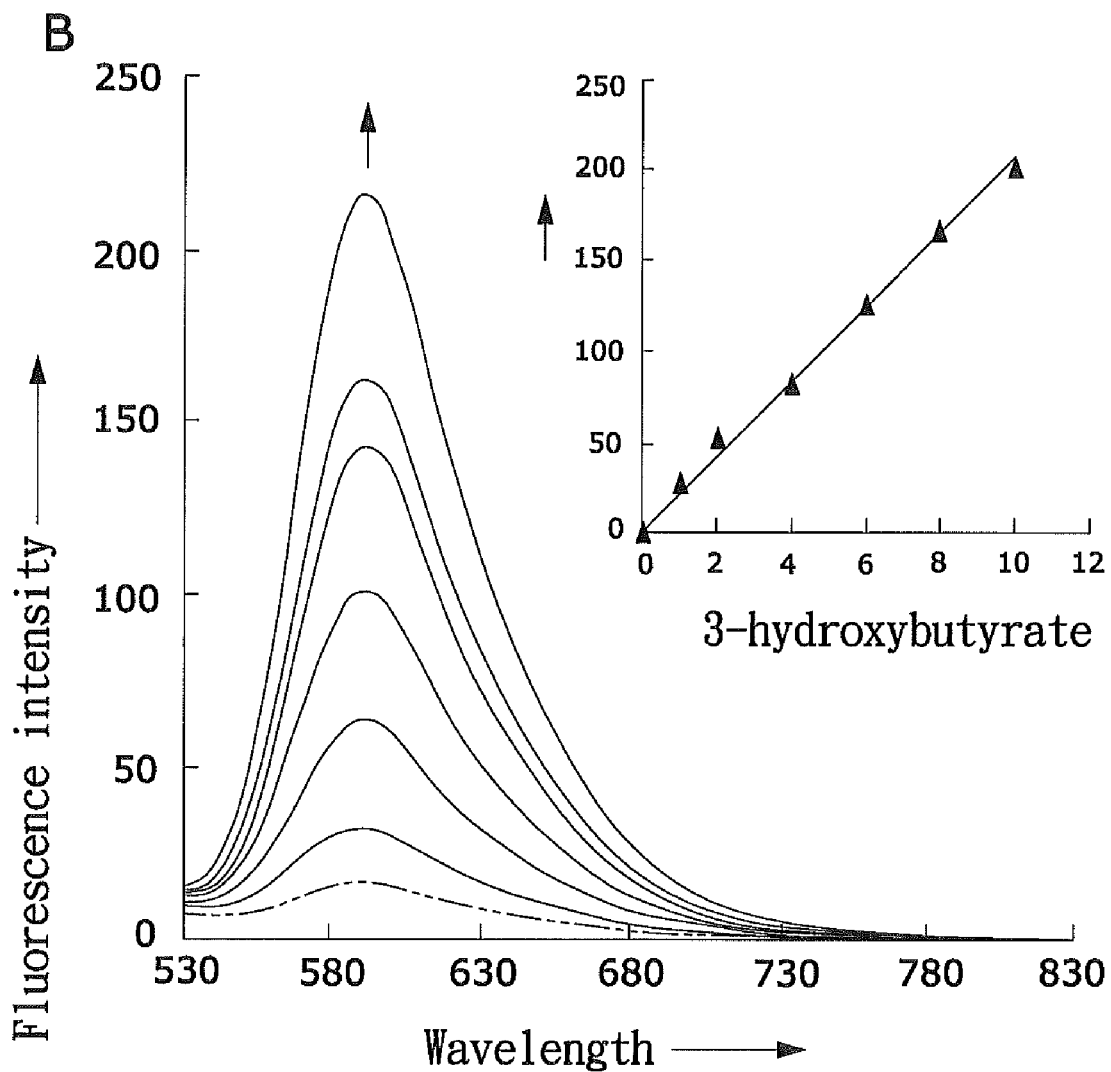
Figure 11:
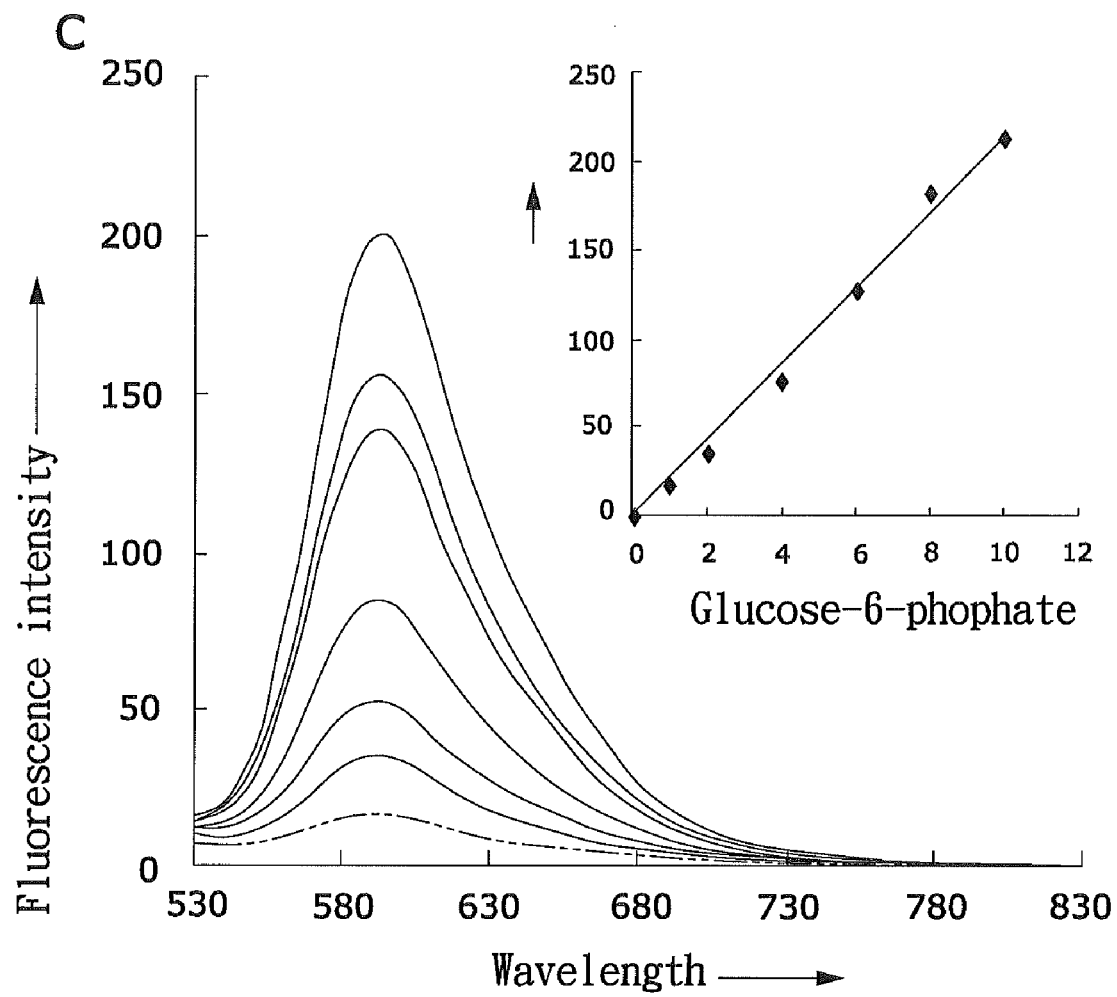

FIG. 7 Excitation and emission spectra of the latent fluorimetric indicator used in the present invention with DT Diaphorase but without NADH FIG. 8 Synthetic scheme of the latent fluorimetric indicator used in the present invention FIG. 9 Fluorescence spectra and fluorescent intensity versus variation of concentration for ethanol using latent fluorimetric indicator of the present invention FIG. 10 Fluorescence spectra and fluorescent intensity versus variation of concentration for 3-hydroxybutyrate using latent fluorimetric indicator of the present invention FIG. 11 Fluorescence spectra and fluorescent intensity versus variation of concentration for glucose-6-phophate using latent fluorimetric indicator of the present invention

DETAILED DESCRIPTION OF THE PREFERRED EMBODIMENTS

<Synthesis Method of Amide (8)>

Refer to the reaction shown in FIG. 8, the mono BOC protected amine (7) (0.2712 g, 1.584 mmol) was dissolved in a solution of $Et_3N$ (0.6 ml) in 4 mL of DMF. In a separate flask, EDCI (0.607 g, 3.168 mmol) and HOBT (0.428 g, 3.168 mmol) was introduced to a solution of benzoquinone acid (6) (0.748 g, 1.584 mmol) in 6 mL of DMF and stirred for 1 h. The resulting mixture was then added dropwise to the mono BOC protected amine (7) solution at room temperature. After 10 h, the solution was diluted with ethyl acetate (50 mL) and washed with water (3×50 mL) and dried with $MgSO_4$, and the solvent was evaporated under reduced pressure. The crude material was purified by flash chromatography (ethyl acetate/dichloromethane, 1:7, $R_f$=0.35) to afford the desired compound as an oil (0.491 g, 1.16 mmol, 74% yield). $^1$HNMR (500 MHz, $CDCl_3$): δ=3.38 (s, 2H), 3.35 (s, 1H), 2.97 (s, 3H), 2.88 (s, 1H), 2.82 (s, 3H), 2.10 (s, 3H), 1.90 (s, 8H), 1.44 (s, 15H). $^{13}$C NMR (125 MHz, CDCl3) δ=191.2, 187.6, 172.1, 154.6, 143.2, 137.9, 136.1, 79.5, 47.5, 47.2, 46.7, 37.6, 37.4, 36.2, 34.9, 28.6, 28.4, 14.1, 12.6, 12.0. MS (EI) $C_{23}H_{36}N_2O_5$ [M+]: m/z=420.5.

<Synthesis Method of Removing BQC Protection Group and Forming Amine (9)>

Refer to the reaction shown in FIG. 8, a solution of amide (8) (0.292 g, 0.694 mmol) and trifluoroacetic acid (0.081 g, 0.718 mmol) in 1.5 mL of $CH_2Cl_2$ was stirred for 3 hours. After 3 hours, the solution was evaporated under reduced pressure. The crude material was purified by flash chromatography (ethyl acetate/dichloromethane, 1:2, then $CH_3OH$ 100%) to afford the desired compound as an oil (0.281 g, 0.647 mmol, yield 93%). $^1$HNMR (500 MHz, $CDCl_3$): δ=3.50 (s, 2H), 3.0~2.91 (m, 5H), 2.57 (s, 3H), 2.0~1.95 (m, 5H), 1.85 (s, 3H), 1.80 (s, 3H), 1.32 (s, 6H). $^{13}$C NMR (125 MHz, CDCl3) δ=191.3, 187.5, 172.1, 154.8, 143.2. 137.9, 136.0, 49.5, 47.7, 47.0, 37.4, 36.1, 33.4, 28.6, 14.1, 12.5, 12.1. MS (EI) $C_{18}H_{29}N_2O_3$ [M+1]: m/z=321.7.

<Synthesis of BQC>

In a two-necked round-buttoned flask (25 mL), a mixture consisting of coumarin (3) (0.834 g, 2.6 mmol), $Et_3N$ (0.361 mL, 2.6 mmol) and THF (10 mL) was prepared. Then trichloromethyl chloroformate (0.078 mL, 0.646 mmol) in THF (5 mL) was added dropwise to the flask. The reaction mixture was stirred for 0.5 h under a stream of Argon at reflux. After 0.5 h, the solution was then poured into methanol and the precipitate was filtered off and vacuum dried. The dicoumarin carbonate (3) was a yellow solid (1.38 g, 2.08 mmol, yield 80%). It was used in the next step without further purification.

In a two-necked round-buttoned flask (25 mL), a mixture consisting of amine (9) (0.823 g, 1.845 mmol), and dicoumarin carbonate (3) (0.9 g, 1.875 mmol) and DMF (2 mL) was prepared. Then $Et_3N$ was added dropwise to the flask. The mixture was reaction for 5 h under a stream of Argon at room temperature. After 5 h, the solution was diluted with ethyl acetate (50 mL) and washed with water (3×50 mL) and dried with $MgSO_4$, and the solvent was evaporated under reduced pressure. The crude material was purified by flash chromatography (IPA/Hexane, 1:5, $R_f$=0.3) to afford the desired compound as yellow solid (1.06 g, 1.59 mmol, yield 85%). mp=147° C. $^1$H NMR (500 MHz, $CDCl_3$): δ=8.23 (d, J=8.0 Hz, 1H), 8.12 (d, 1H), 8.00 (d, J=8.0 Hz, 1H), 7.57 (t, J=7.4 Hz, 1H), 7.50 (t, J=7.4 Hz, 1H), 7.35 (t, 2H), 3.55 (s, 2H), 3.46 (s, 1H), 3.11~3.20 (m, 3H), 3.07 (s, 2H), 3.05 (s, 1H), 2.9 (s, 1H), 2.13 (s, 3H), 1.92 (s, 8H), 1.418 (s, 6H). $^{13}$C NMR (125 MHz, CDCl3) δ=191.1, 187.5, 172.6, 158.2, 156.1, 155.9, 154.3, 153.3, 152.7, 152.1, 142.9, 138.2, 137.5, 136.6, 128.4, 126.9, 126.8, 124.3, 123.5, 121.5, 120.1, 120.0, 114.2, 113.3, 110.3, 47.4, 46.8, 44.5, 37.4, 35.8, 35.3, 28.6, 14.2, 12.6, 12.1. MS (FAB) $C_{36}H_{34}N_4O_7S$ [M+H] m/z=667

Synthesis of Other Types BQC

In the above stated synthesis of BQC, the dicoumarin carbonate (3) part is replaced by other corresponding reactant composition as Eq. (2), Eq. (3), and Eq. (4). And the benzoquinone acid (6) part of the initial reactant could also be replaced by other corresponding reactant composition as Eq. (5) and Eq. (6). And the synthesis procedure follows aforesaid BQC synthesis procedure to complete the synthesis of other types BQC.

<Oxygen-Insensitive Coupling-Enzyme Assay for Analyte Determination>

All the fluorimetric measurements carried out with an excitation wavelength of $\lambda_{ex}$=500 nm and an emission wavelength of $\lambda_{em}$=595 nm. The solutions containing BQC (10 μM), DTD (1 unit), and the corresponding dehydrogenase (1 to 10 unit), $NAD^+$ (10 μM), and ethanol, 3-hydroxybutrate or glucose-6-phosphate (0 to 10 μM) in Tris-HCl buffer with a final volume of 1 mL were incubated for 4 h at 37° C. The fluorimetric intensity of each solution after subtracting the baseline intensity ([analytes]=0) was plotted versus the analytes concentration.

All different ethanol concentration analytes are tabulated in the table below, and the environment of assay is maintained in pH 7.6 at 37° C.

| | Composition | | | |
|---|---|---|---|---|
| S/N | BQC | TrisHCl Buffer with 1% DMSO | NAD⁺ | Enzymes |
| 1 | 10 μM | 50 mM | 10 μM | 10 units of alcohol dehydrogenase and 1 unit of DT Diaphorase |
| 2 | 10 μM | 50 mM | 10 μM | 10 units of alcohol dehydrogenase, 1 unit of DT Diaphorase, and 0.2 μM of ethanol |
| 3 | 10 μM | 50 mM | 10 μM | 10 units of alcohol dehydrogenase, 1 unit of DT Diaphorase, and 0.6 μM of ethanol |
| 4 | 10 μM | 50 mM | 10 μM | 10 units of alcohol dehydrogenase, 1 unit of DT Diaphorase, and 0.8 μM of ethanol |
| 5 | 10 μM | 50 mM | 10 μM | 10 units of alcohol dehydrogenase, 1 unit of DT Diaphorase, and 1 μM of ethanol |
| 6 | 10 μM | 50 mM | 10 μM | 10 units of alcohol dehydrogenase, 1 unit of DT Diaphorase, and 2 μM of ethanol |

All different 3-hydroxybutyrate concentration analytes are tabulated in the table below, and the environment of assay is maintained in pH 7.6 at 37° C.

| | Composition | | | |
|---|---|---|---|---|
| S/N | BQC | TrisHCl Buffer with 1% DMSO | NAD⁺ | Enzymes |
| 1 | 10 μM | 50 mM | 10 μM | 10 units of 3-hydroxybutyrate dehydrogenase and 1 unit of DT Diaphorase |
| 2 | 10 μM | 50 mM | 10 μM | 10 units of 3-hydroxybutyrate dehydrogenase, 1 unit of DT Diaphorase, and 1 μM of hydroxybutyrate |
| 3 | 10 μM | 50 mM | 10 μM | 10 units of 3-hydroxybutyrate dehydrogenase, 1 unit of DT Diaphorase, and 2 μM of hydroxybutyrate |
| 4 | 10 μM | 50 mM | 10 μM | 10 units of 3-hydroxybutyrate dehydrogenase, 1 unit of DT Diaphorase, and 4 μM of hydroxybutyrate |
| 5 | 10 μM | 50 mM | 10 μM | 10 units of 3-hydroxybutyrate dehydrogenase, 1 unit of DT Diaphorase, and 6 μM of hydroxybutyrate |
| 6 | 10 μM | 50 mM | 10 μM | 10 units of 3-hydroxybutyrate dehydrogenase, 1 unit of DT Diaphorase, and 8 μM of hydroxybutyrate |
| 7 | 10 μM | 50 mM | 10 μM | 10 units of 3-hydroxybutyrate dehydrogenase, 1 unit of DT Diaphorase, and 10 μM of hydroxybutyrate |

All different glucose-6-phophate concentration analytes are tabulated in the table below, and the environment of assay is maintained in pH 7.6 at 37° C.

| | Composition | | | |
|---|---|---|---|---|
| S/N | BQC | TrisHCl Buffer with 1% DMSO | NAD⁺ | Enzymes |
| 1 | 10 μM | 50 mM | 10 μM | 10 units of glucose-6-phosphate dehydrogenase, 1 unit of DT Diaphorase, and 2 units of phosphoglucomutase |
| 2 | 10 μM | 50 mM | 10 μM | 10 units of glucose-6-phosphate dehydrogenase, 1 unit of DT Diaphorase, 2 units of phosphoglucomutase, and 1 μM glucose-6-phosphate |
| 3 | 10 μM | 50 mM | 10 μM | 10 units of glucose-6-phosphate dehydrogenase, 1 unit of DT Diaphorase, |

-continued

| | | Composition | | |
|---|---|---|---|---|
| S/N | BQC | TrisHCl Buffer with 1% DMSO | NAD⁺ | Enzymes |
| 4 | 10 μM | 50 mM | 10 μM | 2 units of phosphoglucomutase, and 2 μM of plus glucose-6-phosphate 10 units of glucose-6-phosphate dehydrogenase, 1 unit of DT Diaphorase plus 2 units of phosphoglucomutase, and 4 μM of glucose-6-phosphate |
| 5 | 10 μM | 50 mM | 10 μM | 10 units of glucose-6-phosphate dehydrogenase, 1 unit of DT Diaphorase, 2 units of phosphoglucomutase, and 6 μM of plus glucose-6-phosphate |
| 6 | 10 μM | 50 mM | 10 μM | 10 units of glucose-6-phosphate dehydrogenase, 1 unit of DT Diaphorase, 2 units of phosphoglucomutase, and 8 μM of glucose-6-phosphate |
| 7 | 10 μM | 50 mM | 10 μM | 10 units of glucose-6-phosphate dehydrogenase, 1 unit of DT Diaphorase, 2 units of phosphoglucomutase, and 10 μM of glucose-6-phosphate |

The fluorimetric measurements of different concentration ethanol, 3-hydroxybutyrate, and glucose-6-phosphate analytes are tabulated in Table 1, 2, 3 below and the FIGS. 9, 10, 11:

TABLE 1

| | Ethanol [μM] | | | | | |
|---|---|---|---|---|---|---|
| | 0 | 0.2 | 0.6 | 0.8 | 1 | 2 |
| relative fluorescence intensity | 0 | 10.79 | 26.18 | 35.23 | 39.42 | 77.06 |

TABLE 2

| | 3-Hydroxybutyrate [μM] | | | | | |
|---|---|---|---|---|---|---|
| | 0 | 1 | 2 | 4 | 6 | 8 | 10 |
| relative fluorescence intensity | 0 | 16.17 | 47.59 | 83.74 | 126.26 | 144.93 | 198.56 |

TABLE 3

| | Glusose-6-phosphate [μM] | | | | | | |
|---|---|---|---|---|---|---|---|
| | 0 | 1 | 2 | 4 | 6 | 8 | 9 | 10 |
| relative fluorescence intensity | 0 | 17.02 | 36.84 | 76.41 | 144.45 | 175.2 | 190.32 | 207.94 |

From the FIG. 9 to FIG. 11, it could be clearly seen that either ethanol, 3-hydroxybutyrate or glucose-6-phosphate analytes all have a good linear relationship between the intensity of the fluorescence signal and the variation of concentration. In one aspect, by using the latent fluorimetric probe of the present invention can correctly estimate the concentration of the analytes without any complication. In addition, the diversities of analytes can be varies such as ethanol, 1-propanol, 2-propanol, cyclohexanol, 2-methyl-1-propanol, 1-heptanol, and other primary or secondary alcohols, formaldehyde, acetaldehyde, propyl aldehyde and other alkyl or aromatic aldehyde, lactate, pyruvate, α-ketoglutarate, isocitrate, L-malate, glucose-6-phophate, hydroxybutyrate or another composition in biological samples that have the corresponding dehydrogenase. And the relationship between fluorescence intensity to concentration also has a linear variation result.

While the invention has been described in conjunction with a limited number of embodiments, it will be appreciated by those skilled in the art that many alternative, modifications and variations in light of the foregoing description are possible. Accordingly, the present invention is intended to embrace all such alternative, modifications and variations as may fall within the spirit and scope of the invention as disclosed.

The invention claimed is:

1. A latent fluorimetric probe, wherein the said latent fluorimetric probe is used for detecting the variation of concentration in an object under test, and wherein said latent fluorimetric probe has the structure of Eq. (1):

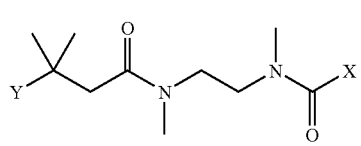

(1)

wherein the structure X of said latent fluorimetric probe has the structure of Eq. (2):

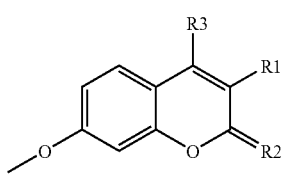

(2)

wherein R1 is a function group selected from

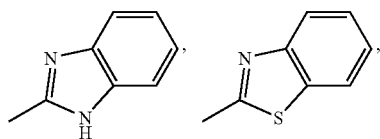

COOH, H, and Cl;

wherein R2 is a function group selected from NH and O; wherein R3 is a function group selected from H and CH$_3$; or wherein said structure X represents the structures of Eq. (3) or and Eq. (4) shown below:

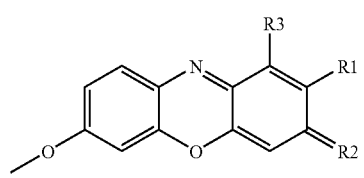

(3)

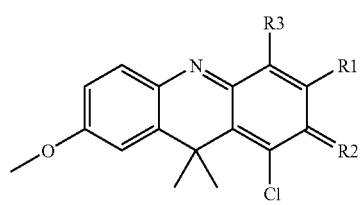

(4)

wherein R1 is a function group selected from

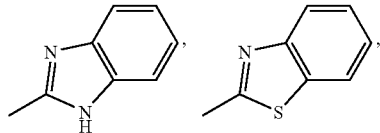

COOH, H, and Cl;

wherein R2 is a function group selected from NH and O; wherein R3 is a function group selected from H and CH$_3$; and wherein the structure Y of the fluorogenic probe has one of the structures of Eq. (5) or Eq. (6) shown below:

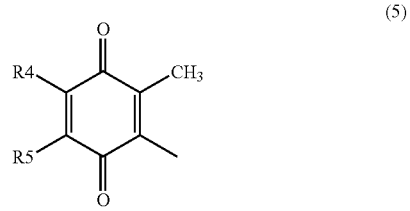

(5)

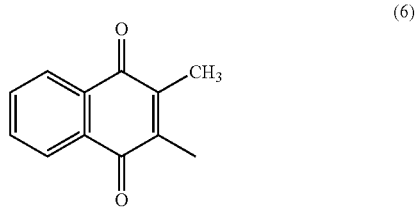

(6)

wherein R4 and R5 is each a function group selected from COOH, H, Cl, and CH$_3$(CH$_2$)$_n$, and n is between 0 and 9.

2. The latent fluorimetric probe according to claim 1, wherein said fluorogenic probe is at least one of a coumarin derivative and a material with a fluorescence feature.

* * * * *